United States Patent [19]

Haag et al.

[11] 4,326,994
[45] Apr. 27, 1982

[54] ENHANCEMENT OF ZEOLITE CATALYTIC ACTIVITY

[75] Inventors: Werner O. Haag, Lawrenceville, N.J.; Rudolph M. Lago, Yardley, Pa.

[73] Assignee: Mobil Oil Corporation, New York, N.Y.

[21] Appl. No.: 121,339

[22] Filed: Feb. 14, 1980

[51] Int. Cl.³ .................... B01J 29/28; B01J 29/06
[52] U.S. Cl. .................................................. 252/455 Z
[58] Field of Search ................................. 252/455 Z

[56] References Cited

U.S. PATENT DOCUMENTS

| | | | |
|---|---|---|---|
| 3,308,069 | 3/1967 | Wadlinger et al. | 252/455 Z |
| 3,493,490 | 2/1970 | Plazik et al. | 252/455 Z |
| 3,541,027 | 11/1970 | Lapides | 252/455 Z |
| 3,700,585 | 10/1972 | Chen et al. | 252/455 Z |
| 3,758,403 | 9/1973 | Rosinski et al. | 252/455 Z |
| 3,766,056 | 10/1973 | Young | 252/455 Z |
| 4,016,218 | 4/1977 | Haag et al. | 260/671 |
| 4,021,447 | 5/1977 | Rubin et al. | 260/326.8 |
| 4,083,889 | 4/1978 | Caesar et al. | 260/682 |

FOREIGN PATENT DOCUMENTS

| | | |
|---|---|---|
| 882681 | 10/1971 | Canada . |
| 2089354 | 12/1971 | France . |
| 2348153 | 4/1976 | France . |
| 2312478 | 5/1976 | France . |
| 1394979 | 5/1975 | United Kingdom . |

*Primary Examiner*—Carl F. Dees
*Attorney, Agent, or Firm*—Charles A. Huggett; Michael G. Gilman; Stanislaus Aksman

[57] ABSTRACT

A method is provided for increasing the catalytic activity of acid zeolite catalysts characterized by a silica to alumina mole ratio of at least 12 and a constraint index within the approximate range of 1 to 12, comprising contacting said zeolite catalysts with water for a sufficient treating time, temperature and water partial pressure to bring about said increased activity. The increase in catalytic activity is within a zone of enhanced activity, said zone is defined as encompassing all those conditions of treating time, temperature and water partial pressure and combinations thereof which yield catalytic activities greater than initial catalyst activity. The zeolite of enhanced activity of the method of the present invention can be utilized in improved acid catalyzed hydrocarbon conversion processes such as cracking, hydrocracking, alkylation, dealkylation, transalkylation, isomerization, dimerization, oligomerization, polymerization, addition, disproportionation, aromatization and hydration.

17 Claims, 1 Drawing Figure

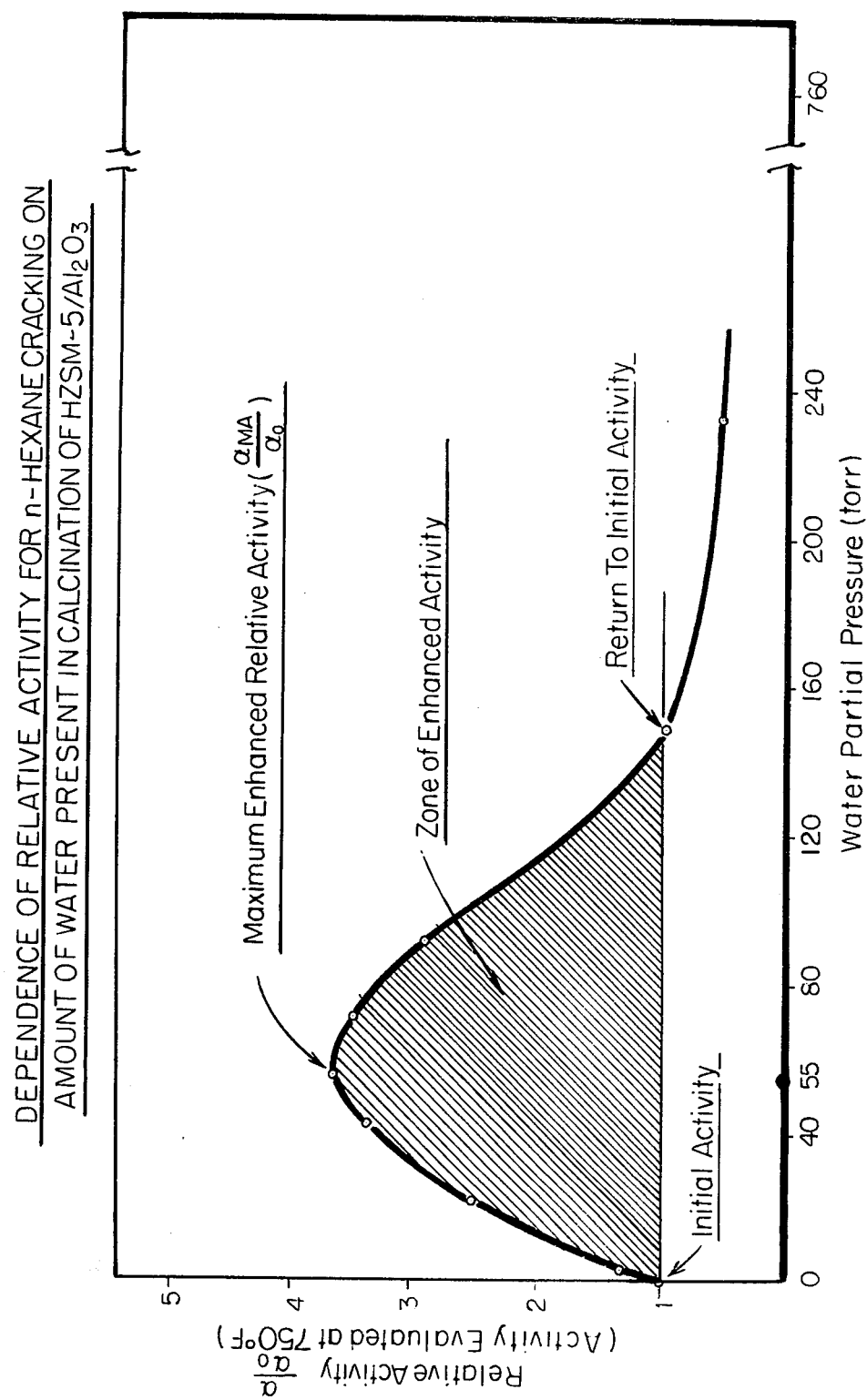

ENHANCEMENT OF ZEOLITE CATALYTIC ACTIVITY

BACKGROUND OF THE INVENTION

1. Field of the Invention

This invention relates to a method for substantially increasing the acid catalytic activity of members of a unique class of crystalline zeolites by treatment with water under controlled conditions.

2. Description of the Prior Art

It is known in the art that the use of steam (water) and/or ammonia can be utilized to modify the activity of acid catalysts, e.g. clays, silica-aluminas and zeolites. Much of the emphasis in the field of catalyst activity modification has been directed towards reducing the activity of catalysts. For example, U.S. Pat. No. 4,016,218 teaches the reduction of catalytic activity of a class of zeolites having a silica to alumina mole ratio of at least 12 and a constraint index within the approximate range of 1 to 12 by the use of prior thermal treatment. Such prior thermal treatment includes the use of a steam atmosphere. It is also known that the use of ammonia can suppress an initially high activity catalyst.

Hydrogen zeolites of the 1 to 12 constraint index type are generally prepared from their alkyl ammonium and ammonium form precursors by calcining in an inert atmosphere, usually in nitrogen at about 1000° F. The more costly nitrogen atmosphere is chosen over the cheaper heating in air to avoid temperature runaway and steam formation that is known to damage the catalyst and results in lower activity. Small samples in the laboratory can be calcined in air without significant steam damage if the temperature is controlled by a slow heat up and by allowing any steam formed to diffuse away. With this careful first calcination, hydrogen zeolites result that are free of residual nitrogen compounds and have the maximum number of acidic hydroxyl groups, which is equal to the number of framework aluminums. Samples thusly prepared are designated "fresh samples". The corresponding catalytic activity of these fresh samples is called "initial activity" and when measured by the alpha ($\alpha$) test as described hereinafter, assigned the designation of "$\alpha$o."

It has long been known that the catalytic activity of hydrogen zeolites can be reduced by high temperature heating and especially by steaming.

It is also known that the deactivation due to steam is pronounced at higher temperatures and longer reaction times. It is also more pronounced at higher steam pressures. Deactivation in the absence of steam, i.e., in an inert atmosphere, requires more severe conditions than steam deactivation.

Recently it has been found that the use of water can be employed to improve certain zeolite catalyst characteristics, while maintaining catalyst activity levels. U.S. Pat. Nos. 4,149,960 and 4,150,062 describe the use of about 0.5 to about 15 moles of water per mole of feedstock in order to substantially reduce the coking and aging rates of the zeolite catalysts used in the processes of these patents.

U.S. Pat. No. 3,493,519 teaches a method of using steam for the stabilization of Y-faujasite zeolite. There, a chelating agent was used after steaming to take out the excess aluminum from the zeolite. The resultant catalyst of this process is a hydrothermally stable zeolite catalyst having high hydrocarbon conversion activity.

In U.S. Pat. No. 3,546,100, it is disclosed that a rare earth exchanged zeolite hydrocracking catalyst such as zeolites X or Y can be improved with respect to its cracking activity and selectivity by using water in controlled amounts to activate catalyst cracking sites. This disclosure states that the amount of water be maintained during the process such that the water vapor partial pressure is kept at a level of about 10 to about 130 mm. water vapor.

SUMMARY OF THE INVENTION

In accordance with the present invention, there has now been discovered a method for substantially increasing the acid catalytic activity of members of a unique class of zeolites by treatment with water, i.e. liquid water or steam under controlled conditions. Whereas under prior art methods the activity of a fresh acid zeolite monotonically decreases upon thermal treatment, under the controlled conditions of this invention, there is a considerable increase in activity over the initial activity.

The members of the unique class of zeolites of the present invention are characterized by a silica to alumina mole ratio of at least 12 and a constraint index within the approximate range of 1 to 12. Unlike other catalyst activation methods, water (steam) addition during the catalytic reaction is not a requirement, rather the catalyst is treated prior to use.

The enhanced zeolite activity attainable by the use of the method of this invention is achieved only under carefully controlled conditions. These conditions depend on the interplay of several variables such as temperature, water partial pressure, treating time, nature of zeolite and nature of treating gas. There exists a "zone of enhanced activity" where zeolite activity is increased over initial activity. Under conditions that are too mild, catalyst activation is not obtained. Alternatively, under too severe conditions, the catalyst will undergo deactivation. Under conditions of constant temperature, the following expression approximately describes the relationships of two variables, treating time and water partial pressure:

$$0.01(Pt)_T < (Pt) < 10(Pt)_T$$

where
(Pt)$_T$ = 2.6 × 10$^{-9}$ e 16000/T
P = Water Partial Pressure, atmospheres
t = Treating Time, hours
T = Temperature, °K.

Whereas under prior art methods ammonia is used to suppress catalyst activity, under the controlled water treating conditions of the present invention, ammonia addition yields even higher activities than with water treating alone.

BRIEF DESCRIPTION OF THE DRAWING

The drawing is a plot of relative activity for n-hexane cracking versus water partial pressure in the calcination of HZSM-5/Al$_2$O$_3$.

DESCRIPTION OF PREFERRED EMBODIMENTS

The catalyst used in the method described herein comprises a crystalline zeolite which is a member of a class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina mole ratios, they are very active even when the silica to alumina mole ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of silicon atoms interconnected by oxygen. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intercrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at a 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| ZEOLITE | C.I. |
| --- | --- |
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-23, ZSM-35 and ZSM-38 and other similar materials. U.S. Pat. No. 3,702,886 decribing and claiming ZSM-5 is incorporated herein by reference.

ZSM-11 is more particularly described in U.S. Pat. No. 3,709,979, the entire contents of which is incorporated herein by reference.

ZSM-12 is more particularly described in U.S. Pat. No. 3,832,449, the entire contents of which is incorporated herein by reference.

ZSM-23 is more particularly described in U.S. Pat. No. 4,076,842, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cation in the forming solution may not be absolutely essential to the formation of this type zeolite; however, the presence of these cations does appear to favor the formation of this special type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites are ZSM-5, ZSM-11, ZSM-12, ZSM-23, ZSM-35 and ZSM-38, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index, as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 100 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relative small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5-11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of ammonium form to yield the hydrogen form. In addition to the hydrogen form, other forms of the zeolite wherein the original alkali metal has been reduced to less than about 1.5 percent by weight may be used. Thus, the original alkali metal of the zeolite or introduced hydrogen cations may be replaced by ion exchange with other suitable ions of Groups IB to VIII of the Periodic Table, including, by way of example, nickel, cadmium, copper, zinc, palladium, calcium or rare earth metals.

In practicing the desired method, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in a raw state as orginally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The degree of zeolite catalyst activity for all acid catalyzed reactions can be measured and compared by means of "alpha value" ($\alpha$). The alpha value reflects the relative activity of the catalyst with respect to a high activity silica-alumina cracking catalyst. To determine the alpha value as such term is used herein, n-hexane conversion is determined at a suitable temperature between about 550° F.–1000° F., preferably at 1000° F. Conversion is varied by variation in space velocity such that a conversion level of up to about 60 percent of n-hexane is obtained and converted to a rate constant per unit volume of zeolite and compared with that of silica-alumina catalyst which is normalized to a reference activity of 1000° F. Catalyst activity of the catalysts are expressed as multiple of this standard, i.e. the silica-alumina standard. The silica-alumina reference catalyst contains about 10 percent $Al_2O_3$ and the remainder $SiO_2$. This method of determining alpha, modified as described above, is more fully described in the Journal of Catalysis, Vol. VI, pages 278–287, 1966.

One measure of comparison used to relate catalyst activities is "relative activity." Relative activity is the ratio of the activity of the catalyst after treatment over the initial activity. Thus relative activity can be expressed as follows:

$$\text{Relative Activity} = \frac{\alpha}{\alpha_o}.$$

The relative activity of a catalyst at the point of initial activity is therefore 1 since $$\frac{\alpha}{\alpha_o} = \frac{\alpha_o}{\alpha_o} = 1.$$

The relative activity of a catalyst at the point of maximum enhanced activity can be expressed as follows:

$$\text{Relative Activity} = \frac{\alpha}{\alpha_o} = \frac{\alpha_{MA}}{\alpha_o}.$$

In order to increase the activity of members of this unique class of zeolites, said zeolites are treated with water, e.g. steam, or water, e.g. steam, produced in-situ. Non-limiting examples of water produced in-situ include alcohol dehydration to produce olefins and steam; and hydrocarbon or coke combustion in the presence of oxygen to form carbon oxides and steam.

During treatment, the zeolite should be at least partially in the acidic form, e.g. hydrogen form. Suitable zeolitic forms also include those that are at least partially convertible to the hydrogen form under treatment conditions, e.g. the ammonium form, or alkyl ammonium form.

There exists a narrow range or band of conditions in which zeolite catalyst activity can be enhanced over the initial activity value. Deviations from this band of conditions can result in either non-enhancement of activity (too mild conditions), or alternatively, catalyst deactivation (too severe conditions). Such conditions include temperature, water partial pressure, treating time, nature of the zeolite, and the nature of the treating gas.

This range of conditions can be clearly demonstrated by a plot of relative activity versus a particular variable, e.g. water partial pressure, treating time, etc., with the other conditions being held constant. Such a plot is given by the drawing in which relative activity is plotted against water partial pressure with temperature and treating time being held constant. With increasing water partial pressure, activity is continuously enhanced above initial relative activity until a point of maximum enhanced relative activity is attained $$\left( \frac{\alpha_{MA}}{\alpha_o} \right).$$

Once maximum enhanced relative activity is achieved, the activity begins to decrease with increasing water partial pressure, ultimately back to the same activity as the initial relative activity (same activity as the untreated zeolite, i.e. initial activity). Increasing water partial pressure after this return to initial activity will eventually result in catalyst deactivation (too severe conditions).

Catalyst activation occurs in a limited region of conditions which can be defined as a "zone of enhanced activity". This zone encompasses those conditions which yield activities greater than the initial activity ($\alpha_o$). Thus the zone is that area bounded by the activity of an untreated catalyst-initial activity and the activity of the catalyst when it returns to the initial activity. In terms of relative activities, the zone of enhanced activity is that area bounded by the initial relative activity $$\left( \frac{\alpha_o}{\alpha_o} = 1 \right)$$

and the return to initial relative activity $$\left( \frac{\alpha}{\alpha_o} = 1 \right).$$

The zone of enhanced activity embraces all conditions and combinations thereof yielding activities greater than the initial catalyst activity. One such activity in this zone is the maximum activity. An expression to approximately define this band in relation to two specific variables—treating time and water partial pressure, with temperature held constant is as follows:

$$0.01(Pt)_T < (Pt) < 10(Pt)_T$$

where
 $(Pt)_T = 2.6 \times 10^{-9} \, e \, 16000/T$
 P = Water Partial Pressure, atmospheres
 t = Treating Time, hours
 T = Temperature, °K.

In regard to the condition of zeolite nature, two particular factors can be evaluated. One factor is the specific zeolite employed, such as ZSM-5, ZSM-11, ZSM-12, ZSM-23, ZSM-35, ZSM-38, etc. Another factor is the crystal size of the particular zeolite employed. For the purposes of this disclosure, small crystal size zeolites are those generally of 0.02 to 0.05 microns and large crystal size zeolites are those of generally 0.1 microns and greater.

The use of large crystal size zeolites rather than small crystal size zeolites has the effect of extending the zone of enhanced catalytic activity. Whereas both large and small size zeolites would conform to the above given relationship of $0.01\,(Pt)_T < (Pt) < 10\,(Pt)_T$, for only small size zeolites, the following preferred range is also applicable:

$$0.01(Pt)_T < (Pt) < 1.0(Pt)_T.$$

The extent of the zone of enhanced activity can also be modified by adjustments in the controlled conditions of treating time, temperature and water partial pressure. The interdependence of these variables (controlled conditions) are such that, for example, an increase in water partial pressure, at constant temperature, will lessen the required treating time to attain a certain activity enhancement. Likewise, increasing the temperature, at constant water partial pressure also lessens the required treating time to attain a specific activity enhancement.

The nature of the treating gas is another influential factor in catalyst activity enhancement. The treating gas in all cases contains either steam or steam producing compounds and mixtures. However, when ammonia is a constituent of the treating gas, even greater zeolite maximum activities than those attainable by steam alone can be achieved. Also the zone of enhanced activity is extended. The preferred range for ammonia addition is from about 0.01 to about 10 mole ratio ammonia/steam and more preferably from about 0.1 to about 1.0 mole ratio ammonia/steam.

Zeolites activated in accordance with the present invention are generally useful as catalysts in acid catalyzed hydrocarbon conversion processes over a range of conversion conditions. Such conditions include a reaction temperature of from about 95° to about 1200° F., preferably from about 390° to about 1000° F., a reaction pressure of from atmospheric to about 10,000 psig, preferably from about atmospheric to about 3,500 psig, and a hydrogen/hydrocarbon compound mole ratio of from 0 to about 20, preferably from 0 to about 10. When the conversion is conducted in a flow apparatus, e.g. a down-flow reactor, or under conditions comparable to those existing in a flow apparatus, the weight hourly space velocity (WHSV) should be maintained at between about 0.1 hr$^{-1}$ and about 1000 hr$^{-1}$, preferably between about 0.5 hr$^{-1}$ and about 10 hr$^{-1}$. When the conversion is conducted in a batch apparatus, e.g. a stirred batch reactor, or under conditions comparable to those existing in a batch apparatus, the contact time should be maintained at between about 0.01 hour and about 48 hours, preferably between about 0.1 hour and about 24 hours.

The subject catalysts have extremely high cracking activity and may be used to convert materials such as gas oils, fuel petroleum crudes, paraffins, olefins and the like from high to low molecular weight substances. The activated catalysts produced by the instant invention may also be used in hydrocracking, alkylation, dealkylation, transalkylation, isomerization, dimerization, oligomerization, polymerization, addition, disproportionation, aromatization, hydration and many other acid catalyzed reactions. A typical alkylation reaction involves the use of aromatics and olefins to synthesize such materials as ethylbenzene, ethyltoluene, or cumene. Another alkylation reaction involves the use of aromatics and paraffins. A typical transalkylation reaction involves reacting benzene and methylnaphthalene to form toluene and naphthalene. Another transalkylation reaction is the conversion of toluene and trimethylbenzene to xylenes. Typical disproportionation reactions include the conversion of toluene to benzene and xylenes or the conversion of methylnaphthalene to naphthalene and dimethylnaphthalenes. Isomerization reactions may be carried out with diverse feedstocks such as paraffins, olefins or alkyl aromatics, e.g. xylenes.

In particular, when the conversion of hydrocarbon compounds by the present method is olefin polymerization, catalytic conversion conditions should be maintained within certain ranges, including a temperature of from about 95° to about 935° F., preferably from about 390° F. to about 810° F., a pressure of from about atmospheric to about 10,000 psig, preferably from about atmospheric to about 2,000 psig, a WHSV (when a flow operation) of from about 0.1 hr$^{-1}$ to about 1000 hr$^{-1}$, preferably from about 0.5 hr$^{-1}$ to about 100 hr$^{-1}$, and a contact time (when a batch operation) of from about 0.1 hour to about 48 hours, preferably from about 0.5 hour to about 24 hours and a hydrogen/hydrocarbon (i.e. olefin) mole ratio of from about 0 to about 20, preferably from about 0 to about 10.

When the conversion is olefin or paraffin aromatization, catalytic conversion conditions should be maintained within certain ranges, including a temperature of from about 550° F. to about 1200° F., preferably from about 650° F. to about 1100° F., a pressure of from about atmospheric to about 10,000 psig, preferably from about atmospheric to about 2000 psig, a WHSV (when a flow operation) of from about 0.1 hr$^{-1}$ to about 10 hr$^{-1}$, preferably from about 1 hr$^{-1}$ to about 5 hr$^{-1}$, a contact time (when a batch operation) of from about 0.1 hour to about 48 hours, preferably from about 1 hour to about 24 hours and a hydrogen/hydrocarbon, i.e. olefin or paraffin, mole ratio of from about 0 to about 20, preferably from about 0 to about 10.

Further, when the conversion of hydrocarbon compounds by the present process is cracking, catalytic conversion conditions should be maintained within certain ranges, including a temperature of from about 700° to about 1200° F., preferably from about 800° to about 1100° F., a pressure of from about atmospheric to about 200 psig, a WHSV (when a flow operation) of from about 0.5 hr$^{-1}$ to about 50 hr$^{-1}$, preferably from about 1 hr$^{-1}$ to about 10 hr$^{-1}$, and a contact time (when a batch operation) of from about 0.01 hour to about 24 hours, preferably from about 0.1 hour to about 10 hours. When the conversion is hydrocracking, catalytic conversion conditions should be maintained within somewhat different ranges, including a temperature of from about 400° to about 1000° F., preferably from about 500° to about 850° F., a pressure of from about 500 psig to about 3500 psig, a WHSV (when a flow operation) of from about 0.1 hr$^{-1}$ to about 10 hr$^{-1}$, preferably from about 0.2 hr$^{-1}$ to about 5 hr$^{-1}$, a contact time (when a batch operation) of from about 0.1 hour to about 10 hours, preferably from about 0.2 hour to about 5 hours and a hydrogen/hydrocarbon mole ratio of from about 1 to about 20, preferably from about 3 to about 10.

When the conversion of hydrocarbon compounds by the instant process is isomerization, conversion conditions include a temperature of between about 450° F. and about 1000° F., a pressure of between about 0 and about 500 psig, a WHSV of between about 0.1 and 200 hr$^{-1}$, and a hydrogen to hydrocarbon mole ratio of between about 0.1 and about 10.

When the conversion is alkylation or transalkylation by the present process, conversion conditions include a temperature of between about 100° F. and about 950° F. for alkylation and a temperature of between about 650° F. and about 1100° F. for transalkylation, a pressure of between about 0 and about 1000 psig for both alkylation and transalkylation, and a WHSV of between about 1 and about 500 for alkylation and of between about 1 and 20 for transalkylation.

When the conversion is disproportionation by the instant process, conversion conditions include a temperature of between about 650° F. and about 1100° F., a pressure of between about 0 and about 1000 psig, a WHSV of between about 1 and about 20 and a hydrogen to hydrocarbon mole ratio of between about 0 and about 4.

The carrying out of the activity enhancement method of this invention can be accomplished concomitant with zeolite manufacture. Alternatively, a conventionally treated catalyst can be utilized in a particular process with enhancement being brought about later, such as in subsequent cycles, or between cycles.

The following examples will serve to illustrate the process of the present invention without unduly limiting same.

EXAMPLE 1

A "small crystal size" ZSM-5 with a crystal size of about 0.02 to 0.05 microns was prepared as follows:

A sodium silicate solution was prepared by mixing 16.7 parts water and 28.6 parts sodium silicate (28.7 wt % SiO$_2$, 8.9 wt % Na$_2$O, 62.4% H$_2$O) followed by addition of 0.08 parts Daxad 27 (W. R. Grace Chem. Co.) The solution was cooled to approximately 15° C.

An acid solution was prepared by adding 1 part aluminum sulfate (17.2 wt % Al$_2$O$_3$) to 17.1 parts water, followed by 2.4 parts sulfuric acid (93 wt % H$_2$SO$_4$) and 2.7 parts NaCl.

The silicate solution and the acid solution were mixed in an agitated vessel while 2.0 parts of NaCl and 0.8 parts water were added to form a gel.

An organic solution was prepared by adding 1.9 parts tri-n-propylamine, 1.7 parts n-propyl bromide and 3.2 parts methyl-ethyl ketone.

The organic solution was added to the gel and the mixture was reacted at about 220° F. without agitation and held there for 14–15 hours to prereact the organics. At the end of the prereaction period the agitation was commenced to start the initial crystallization period. After about 75–80 hours the temperature was raised to 320° and held there for about three hours to complete crystallization. The excess or unreacted organics were flashed off and the remaining contents were cooled and discharged. The zeolite was then washed and dried.

The product was identified as ZSM-5 with a sodium level of about 0.01 wt % and having a silica to alumina mole ratio of about 70.

After drying, the zeolite was mixed with alpha alumina monohydrate and water to an extrudable consistency and formed into 1/16" extrudates. The extrudates were dried, calcined in flowing N$_2$ for 3 hours at 1000° F. then ion exchanged twice with 1 N NH$_4$NO$_3$ solution (5 parts NH$_4$NO$_3$ solution/1 part zeolite) for 1 hour at ambient temperature and dried.

EXAMPLE 2

A 50 cc sample of ammonium ZSM-5 prepared according to the procedure of Example 1 and containing Al$_2$O$_3$ as a binder material was calcined in an air flow of 1500 cc/min of air to yield a hydrogen form of the zeolite. Aliquot portions of this calcined material were then calcined for 2½ hours at 1000° F. in flowing nitrogen containing various water partial pressures and relative hexane cracking activities were determined at 750° F. for purposes of comparison. The results for this example are shown in Table 1 and graphically shown in the drawing.

TABLE 1

| Steam Partial Pressure (torr) | | Relative Activity for Hexane Cracking at 750° F. |
|---|---|---|
| | 0 | 1.0 (starting material) |
| | 5 | 1.3 |
| zone of | 22 | 2.6 |
| enhanced | 43 | 3.5 |
| activity | 55 | 3.8 (maximum activity) |
| | 72 | 3.6 |
| | 93 | 3.0 |
| | 149 | 1.0 (same activity as starting material) |
| | 234 | 0.61 |
| | 760 | 0.11 |

As can be seen from Table 1 and the drawing, there is a continuous increase in cracking activity with increasing steam pressure until a maximum activity is attained at 55 torr steam. This maximum activity represents about a four fold increase over the starting material. After this maximum activity is achieved, activities decrease with increasing steam pressure, but still remain higher than the starting material up to 149 torr steam.

EXAMPLE 3

Another sample of small crystal ZSM-5 such as that prepared according to Example 1, was treated at 750° F. for 23 hours in one atmosphere steam. The hexane cracking activity of the sample, determined at 1000° F., was increased from an initial activity of $\alpha_0 = 162$ to a maximum activity of $\alpha = 200$.

EXAMPLE 4

A "large crystal size" ZSM-5 with a crystal size of about 1–5 microns was prepared as follows:

A sodium silicate solution was prepared by mixing 16 parts water and 27.7 parts sodium silicate (28.7 wt % SiO$_2$, 8.9 wt % Na$_2$O, 62.4% H$_2$O) followed by addition of 0.08 parts Daxad 27 (W. R. Grace Chem. Co.) The solution was cooled to approximately 15° C.

An acid solution was prepared by adding 1 part aluminum sulfate (17.2 wt % Al$_2$O$_3$) to 16.4 parts water, followed by 2.4 parts sulfuric acid (93 wt % H$_2$SO$_4$) and 1.2 parts NaCl.

These solutions were mixed in an agitated vessel while 3.9 parts of NaCl were added. The gel molar ratios expressed as oxides are the following:

| | | |
|---|---|---|
| SiO$_2$/Al$_2$O$_3$ | = | 78.4 |
| Na$_2$O/Al$_2$O$_3$ | = | 49.9 |

An organic solution was prepared by adding 1.6 parts n-propyl bromide and 3.1 parts methyl-ethyl ketone to 1.9 parts tri-n-propylamine and added to the gel.

The mixture was reacted at 150°–160° F. with severe agitation for 29 hours.

The zeolite slurry product was diluted with 4–5 parts water per part slurry and 0.0002 parts of flocculent (Rohm & Haas Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the decant supernatant liquid was Cl⁻ free. The washed zeolite was then filtered, dried and identified as ZSM-5 having a silica/alumina mole ratio of at least 12; i.e., about 70, and a constraint index of between 1 and 12; i.e., about 8.3.

The dried zeolite product was calcined in flowing $N_2$ for 3 hours at 538° C. then ion exchanged twice with 1 N $NH_4NO_3$ solution (5 parts $NH_4NO_3$ sol'n/1 part zeolite) for 1 hour at ambient temp. and dried at about 120° C.

EXAMPLES 5 to 7

Large crystal size ZSM-5 prepared according to Example 4 and used in its hydrogen form was treated at three different temperatures, all in one atmosphere steam for various amounts of time. Example 5 was conducted at 750° F.; Example 6 was conducted at 800° F. and Example 7 was conducted at 1000° F. Relative activities measured at 1000° F. in terms of alpha values were evaluated for all the time intervals in all three examples. The results for these examples are given in Table 2.

TABLE 2

| Example No. | Temperature °F. | Time, Hours | | Relative Activity $\frac{\alpha}{\alpha_o}$ |
|---|---|---|---|---|
| 5 | 750 | duration of catalyst activation | 0 | 1.00 |
| | | | 23 | 2.41 (maximum point) |
| | | | 70 | 1.31 |
| | | | 170 | 0.51 |
| 6 | 800 | | 0 | 1.00 |
| | | | 1.9 | 1.68 |
| | | | 4 | 2.04 |
| | | | 8 | 2.20 (maximum point) |
| | | | 25 | 2.09 |
| 7 | 1000 | duration of catalyst activation | 0 | 1.00 |
| | | | 2 | 2.68 (maximum point) |
| | | | 3 | 1.16 |
| | | | 3.2 | 1.00 |
| | | | 4 | 0.70 |

In comparing the results of Examples 5, 6 and 7 against each other, the effect of temperature can be evaluated. In increasing the temperature, the time required to reach the maximum relative activity is decreased. At 750° F., the maximum relative activity is achieved after 23 hours, while at 800° F., the maximum relative activity is attained after 8 hours. At 1000° F., only 2 hours is required to attain the maximum relative activity. Consequently, when temperature is increased, the duration of catalyst activation is decreased. At 750° F., the duration of catalyst activation is between 70 hours and 170 hours, while at 1000° F., the duration of catalyst activation is only 3.2 hours. The "duration of catalyst activation" is defined as the amount of treating time required for the catalyst activity to return to its initial value (to a value of relative activity=1).

EXAMPLE 8

ZSM-5 with a crystal size of about 0.1–0.5 microns was prepared as follows:

A sodium silicate solution was prepared by mixing 16 parts water and 27.7 parts sodium silicate (28.7 wt % $SiO_2$, 8.9 wt % $Na_2O$, 62.4% $H_2O$). The solution was cooled to approximately 15° C.

An acid solution was prepared by adding 1 part aluminum sulfate (17.2 wt % $Al_2O_3$) to 16.4 parts water, followed by 2.4 parts sulfuric acid (93 wt % $H_2SO_4$) and 1.2 parts NaCl.

These solutions were mixed in an agitated vessel while 3.9 parts of NaCl were added. The gel molar ratios expressed as oxides are the following:

| | | |
|---|---|---|
| $SiO_2/Al_2O_3$ | = | 78.4 |
| $Na_2O/Al_2O_3$ | = | 49.9 |

An organic solution was prepared by adding 1.6 parts n-propyl bromide and 3.1 parts methyl-ethyl ketone to 1.9 parts tri-n-propylamine.

After the gel was heated to about 95° C., agitation was reduced and the organic solution was added above the gel. This mixture was held at about 95°–110° C. for 14 hours, then agitation increased and the temperature was increased to about 150°–160° C. and held there until crystallization was complete. Unreacted organics were removed by flashing and the remaining contents cooled.

The zeolite slurry product was diluted with 4–5 parts water per part slurry, allowed to settle and supernatant liquid was drawn off. The settled solids were reslurried to the original volume of the preceding step with water. After settling, the aqueous phase was decanted. This procedure was repeated until the sodium level of the zeolite was less than 1.0 wt%. The washed zeolite was then filtered, dried and identified as ZSM-5 having a silica/alumina mole ratio of at least 12; i.e., about 70, and a constraint index of between 1 and 12; i.e., about 8.3.

EXAMPLES 9 and 10

The intermediate size zeolite ZSM-5 prepared according to the procedure of Example 8 and used in its hydrogen form was heated at a rate of 20° C. per minute in a stream of dry helium. This zeolite had an initial activity in terms of alpha value of 211. In Example 9, the HZSM-5 was heated to 1400° F. and held for 2 hours at that temperature. In Example 10, the HZSM-5 was heated to 1800° F. and then rapidly cooled. After treatments according to Example 9 and Example 10, the activities of the zeolite in terms of alpha value were determined. The results are shown in Table 3.

TABLE 3

| Example No. | Final Temperature, °F. | Time Held at Final Temperature, hrs. | Initial Activity $\alpha_o$ | Final Activity $\alpha$ |
|---|---|---|---|---|
| 9 | 1400 | 2 | 211 | 240 |
| 10 | 1800 | 0 | 211 | 300 |

EXAMPLE 11

HZSM-11 was prepared according to the procedure given in Example 6, Table II of U.S. Pat. No. 4,108,881 and was converted to $NH_4ZSM$-11 by the following method:

Three grams of the HZSM-11 was air calcined for 10 hours in a muffle furnace. It was then exchanged twice, at room temperature, with stirring, with 200 ml. of 0.5

N NH$_4$Cl solution for two hours per exchange. It was washed and air dried.

EXAMPLE 12

The NH$_4$ZSM-11 prepared according to the general procedure of Example 11 was heated for 10 hours at 1000° F. in a closed container, thus providing an atmosphere containing both steam and ammonia. This treatment resulted in a 3.1 fold increase in catalytic activity relative to a sample that was treated in an inert atmosphere.

EXAMPLE 13

Another NH$_4$ZSM-11 sample was prepared according to the following procedure:

A sodium silicate solution was prepared by mixing 14.4 parts sodium silicate (28.7 wt % SiO$_2$, 8.9 wt % Na$_2$O, 62.4 wt % H$_2$O) with 8.4 parts water and 0.04 parts Daxad 27 (W. R. Grace Chem. Co.).

An acid solution was prepared by mixing 1 part aluminum sulfate (17.2 wt % Al$_2$O$_3$), 1.4 parts sulfuric acid, 0.8 parts sodium chloride and 6.3 parts water.

The silicate solution and acid solution were combined in a mixing nozzle and the resulting gel discharged into an agitated vessel to which 0.4 parts of water had been added. The gel was thoroughly mixed at ambient temperature and 0.6 parts of sodium chloride was added to the mixture. Finally, a solution containing 1.4 parts of tetrabutylammonium bromide and 2.1 parts water was added to the mixture. The temperature of the gel mixture was raised to 220° F. with severe agitation and held for 256 hours until crystallization was complete. The crystallized product was cooled, filtered, washed free of soluble salts and dried. The dried product was analyzed by X-ray diffraction and identified as ZSM-11.

EXAMPLE 14

The NH$_4$ZSM-11 prepared according to the general procedure of Example 13 was heated for 10 hours at 1000° F. in a closed container. The treatment resulted in a 4.2 fold increase in catalytic activity relative to a sample treated in an inert atmosphere.

EXAMPLE 15

Zeolite ZSM-12 was prepared according to the following procedure:

A reaction mixture was prepared by mixing 65 parts of Hi-Sil (a precipitated SiO$_2$), 6.3 parts NaOH, 1 part Al(NO$_3$)$_3$.9H$_2$O, 40 parts tetraethylammonium bromide and 310 parts H$_2$O. The mixture was charged to a vessel, thoroughly agitated and heated to about 320° F. and held for about 16 hours with agitation. At this point the reaction mixture was cooled and 1.1 parts of NaAlO$_2$ and 2.7 parts H$_2$O were added. The reaction mixture was reheated to 320° F. and held for an additional 24 hours at 320° F. with agitation to complete crystallization.

The crystallized product was washed and dried and then identified as 90% ZSM-12 by X-ray diffraction with the following chemical analysis:

| | % Wt |
|---|---|
| Al$_2$O$_3$ | 1.79 |
| SiO$_2$ | 95.1 |
| Na | 0.34 |
| N | 0.98 |

-continued

| | % Wt |
|---|---|
| C | 7.63 |

The washed and dried zeolite was calcined in flowing N$_2$ for 3 hours at 1000° F. then ion exchanged three times with 1 N NH$_4$NO$_3$ solution (5 parts NH$_4$NO$_3$ sol'n/1 part zeolite) for 1 hour at ambient temperature and dried at about 250° F.

EXAMPLE 16

A sample of HZSM-12 prepared according to the general procedure of Example 15 was heated in flowing steam of 1 atmosphere pressure at 850° F. for various amounts of time. The results for this example are illustrated in Table 4.

TABLE 4

| Time, hours | Activity |
|---|---|
| 0 | 138 |
| 2 | 308 |
| 5 | 179 |
| 10 | 138 |

EXAMPLE 17

A sample of HZSM-5 prepared according to the general procedure of Example 4 was steam activated for 10 hours at 1000° F. in a closed container. Toluene at a rate of 10 WHSV and 1 atmosphere pressure was passed over both the treated and untreated HZSM-5 catalyst at 900° F. in a vertical flow reactor. Toluene was disproportionated to benzene, xylenes and small amounts of trimethyl benzenes. The results of Example 17 are exhibited in Table 5.

TABLE 5

| CATALYST | TOLUENE CONVERSION |
|---|---|
| Untreated Catalyst | 8.5% |
| Steam Treated Catalyst | 13.0% |

EXAMPLES 18 and 19

In these examples small crystal HZSM-5 with a initial hexane cracking activity of 191 prepared according to the general procedure of Example 1 was utilized. The zeolite in each example was treated with a flowing stream of a particular gas at 1000° F. Results for these examples are given in Table 6.

TABLE 6

| Example No. | Nature of Treating Gas | Change in Activity |
|---|---|---|
| 18 | Helium | None |
| 19 | Helium Containing 6 Vol. % NH$_3$ | 1.7 Fold Increase |

EXAMPLE 20

The experimental procedure and catalyst used in this example were the same as described in Example 2, except that in this example an inert gas stream containing about 3-14 vol. % ammonia was utilized along with the specified partial pressure amounts of steam. After each treatment, the sample was heated in a dry nitrogen stream to 1000° F. to remove adsorbed water and ammonia and the relative activity for cracking hexane was determined at 750° F. The results for Example 20 are given in Table 7.

TABLE 7

| Steam Pressure, (torr) | Relative Activity for Hexane Cracking at 750° F. |
| --- | --- |
| 0 | 1.0 (starting material) |
| 5 | 2.5 |
| 19 | 4.6 |
| 50 | 8.6 |
| 107 | 8.8 (maximum activity) |
| 128 | 7.4 |
| 258 | 4.6 |
| 683 | 1.4 |

While either steam treatment or ammonia treatment alone produce a catalyst with enhanced activity under mild conditions, the simultaneous presence of steam and ammonia has an unexpected additional synergistic effect above that of the individual gases, as shown in Example 20.

As can be seen by a comparison with Example 2, the synergistic action of both steam and ammonia produce catalysts with even greater activity than by steam treatment alone. In Example 2 where only steam is used, the maximum relative activity is 3.8, whereas in this example where ammonia is added to the steam, the maximum relative activity is 8.8. In addition, the range of treating conditions that give enhanced activities, rather than deactivation is increased. For example, under the conditions of time and temperature of Example 2, the range of beneficial steam pressures is increased from 5 to 149 torr for steam to a range of 5 to about 700 torr steam by the addition of small concentrations of ammonia.

What is claimed is:

1. A method for increasing the catalytic activity of an acid zeolite having a determinable initial activity and characterized by a silica to alumina mole ratio of at least 12 and a constraint index within the approximate range of 1 to 12, comprising contacting said zeolite with water for a sufficient treating time, temperature and water partial pressure wherein said time, temperature and pressure is represented by the following relationship of treating time and water pressure at constant temperatures:

$$0.01(Pt)_T < (Pt) < 10(Pt)_T$$

where $(Pt)_T = 2.6 \times 10^{-9} e^{16000/T}$

P = Water Partial Pressure, atmosphere t = Treating Time, Hours

T = Temperature, °K.

2. The method of claim 1 wherein said zeolite is selected from the group consisting of ZSM-5, ZSM-11, ZSM-12, ZSM-23, ZSM-35 and ZSM-38.

3. The method of claim 1 wherein said zeolite is in the hydrogen form.

4. The method of claim 1 wherein said zeolite is in the ammonium form.

5. The method of claim 1 wherein said water is liquid water.

6. The method of claim 1 wherein said water is steam.

7. The method of claims 5 or 6 wherein said water is produced in-situ.

8. The method of claim 7 wherein said water produced in-situ is obtained from alcohol dehydration.

9. The method of claim 7 wherein said water produced in-situ is obtained from hydrocarbon combustion in the presence of oxygen.

10. The method of claim 7 wherein said water produced in-situ is obtained from coke combustion in the presence of oxygen.

11. The method of claim 1 wherein ammonia is added to said water in amounts ranging from between about 0.01 and about 10 mole ratio ammonia to water.

12. The method of claim 11 wherein said ammonia is added in amounts ranging from between about 0.1 and about 1.0 mole ratio ammonia to water.

13. The method of claim 1 wherein a maximum enhanced activity is attained.

14. The method of claim 1 wherein treating time, temperature and water partial pressure are selected such that the increased catalytic activity is within a zone of enhanced activity, said zone being defined as encompassing all those conditions of treating time, temperature and water partial pressure and combinations thereof which yield catalytic activities greater than the initial activity.

15. The method of claim 1 wherein said zeolite has a crystal size of 0.02 to 0.05 microns and said relationship of treating time and water pressure at constant temperature is as follows:

$$0.01(Pt)_T < (Pt) < 1.0(Pt)_T$$

16. The acid zeolite produced by the methods of claims 1, 2, 3, 4, 5, 6, 7, 8, 9, 10, 11, 12, 13, 14, or 15.

17. The process of claim 14 wherein said acid zeolite is composited with a matrix material.

* * * * *

UNITED STATES PATENT AND TRADEMARK OFFICE
CERTIFICATE OF CORRECTION

PATENT NO. : 4,326,994

DATED : April 27, 1982

INVENTOR(S) : Werner O. Haag and Rudolph M. Lago

It is certified that error appears in the above—identified patent and that said Letters Patent is hereby corrected as shown below:

Column 1, line 50          Before "pronounced", insert --more--.

Column 7, line 28          Before "percent", insert --weight--.

Signed and Sealed this

Twenty-seventh Day of July 1982

[SEAL]

Attest:

*Attesting Officer*

GERALD J. MOSSINGHOFF

*Commissioner of Patents and Trademarks*